US006489317B1

(12) United States Patent
Borody

(10) Patent No.: US 6,489,317 B1
(45) Date of Patent: Dec. 3, 2002

(54) **METHOD FOR ERADICATION OF *HELICOBACTER PYLORI***

(76) Inventor: Thomas Julius Borody, 144 Great North Road, Five Dock, NSW 2046 (AU)

( * ) Notice: Subject to any disclaimer, the term of this patent is extended or adjusted under 35 U.S.C. 154(b) by 0 days.

(21) Appl. No.: 09/673,631

(22) PCT Filed: Apr. 30, 1999

(86) PCT No.: PCT/AU99/00321

§ 371 (c)(1),
(2), (4) Date: Nov. 20, 2000

(87) PCT Pub. No.: WO99/56749

PCT Pub. Date: Nov. 11, 1999

(30) Foreign Application Priority Data

Apr. 30, 1998 (AU) .............................. PP3253

(51) Int. Cl.[7] ...................... A61K 31/43; A61K 31/166; A61K 31/4439; A61K 31/4525; A61K 33/24
(52) U.S. Cl. ...................... 514/197; 514/192; 514/278; 514/338; 514/395; 514/503; 514/619; 514/819; 514/925; 514/926; 514/927; 514/928; 424/653
(58) Field of Search ................................. 514/192, 278, 514/338, 395, 619, 503, 197, 819, 925, 926, 927, 928; 424/653

(56) References Cited

FOREIGN PATENT DOCUMENTS

| WO | WO 97/02039 | 1/1997 |
| WO | WO 98/43667 | 12/1998 |

OTHER PUBLICATIONS

MEDLINE Abstract, accession No. 2000485341, Oct. 2000.*
Chemical Abstract 132:260474, 2000.*
EMBASE Abstract, accession No. 2001187096, 2000.*
Perri, F. et al., "Treatment of Antibiotic–Resistant *Helicobacter pylori* Infection", The New England Journal of Medicine, vol. 339, No. 1, p. 53, Jul. 1998.*
Vaira, D., et al., Curr. Ther. Res. 58(5), 300–308 (5/97).
Holton, J., et al., J. Antimicrob. Chemother. 35(4), 545–549 (4/95).
Kunin, C. M., Clin. Infect. Dis. 22 (Suppl. 1), S3–S14 (4/96).
Gevaudan, M. J., et al., Pathol. Biol. (Paris) 39(5), 436–441 (5/91).
Shafran, S. D., et al., N. Engl. J. Med. 335(6), 377–383 (Aug. 8, 1996).
Yaiko, D. M., et al., Antimicrob. Agents Chemother. 40(3), 743–749, 3/96.
De Giorgio, R., et al., European Review for Medical and Pharmacological Sciences, vol. 1, No. 4, 105–110, 7/97.

* cited by examiner

*Primary Examiner*—John Pak

(57) ABSTRACT

The invention provides methods for the treatment and/or prevention of recurrence of a gastrointestinal disorder associated with *Helicobacter pylori* in a patient requiring said treatment and/or prevention, which comprise administering to the patient a therapeutically effective amount of a first antibiotic which is an ansamycin and a therapeutically effective amount of at least a second antibiotic or antimicrobial agent. The invention also provides pharmaceutical compositions for use in the methods of the invention.

18 Claims, No Drawings of chronic gastritis and peptic ulcer disease, such as gastric
METHOD FOR ERADICATION OF HELICOBACTER PYLORI This application is a 371 of PCT/AU99/00321, filed on Apr. 30, 1999.

TECHNICAL FIELD

This invention relates to pharmaceutical compositions and therapeutic methods for the treatment and/or prevention of recurrence of gastrointestinal disorders associated with infection by Helicobacter pylori (H. pylori).

BACKGROUND

Helicobacter pylori has been found to cause chronic histological gastritis and peptic ulcer disease, such as gastric and duodenal ulcer. It also appears to cause a condition called non-ulcer dyspepsia where Helicobacter pylori causes inflammation in the stomach which is histologically associated with indigestion and epigastric pain. Helicobacter pylori is also thought to have a role in the causation of stomach cancer and its eradication may be instrumental in causing cure of ulcer disease, a reversal of a proportion of patients with non-ulcer dyspepsia, and prevention of gastric cancer development in those who may be predisposed to it.

Until recent times, H. pylori has been found to be difficult to eradicate using known chemotherapeutic agents. Although many antibiotics can suppress H. pylori growth in vivo the mucosal concentration appears to be inadequate and penetration of the usual gastric mucus layer is poor. Furthermore, there is frequently more than one infecting agent within the mucosa and hence, sensitivities of the various bacteria may vary within one patient and within one region of the mucosa. The development of adequate in vivo eradication methods for chronic H. pylori infection has therefore been difficult. Furthermore, single antibiotics are almost never adequate for use and double antibiotic combinations have also resulted in poor eradication rates. A further major looming problem progressively affecting current eradication therapies is the rapid development of clarithromycin resistance worldwide. The proportion of H. pylori infections which are resistant to clarithromycin is increasing by from 2–5% per year. Resistance is developing faster in the countries where clarithromycin is being used frequently; in particular, USA and Europe. Hence, new methods for eradication of H. pylori are urgently required. In addition, salvage therapies for patients who have failed first time therapy are also unavailable and such treatments are becoming in demand as more and more patients undergo therapy and fail initial eradication attempts.

It is therefore an object of the present invention to provide a novel pharmaceutical composition for the treatment and/or prevention of recurrence of gastrointestinal disorders associated with H. pylori.

It is a further object of the invention to provide methods for the treatment and/or prevention of recurrence of a gastrointestinal disorder associated with H. pylori in a patient.

DISCLOSURE OF THE INVENTION

The present inventor has found that the use of a novel combination antibiotic therapy not only results in high initial eradication rates of H. pylori but also can be used as a salvage therapy. There is a large volume of literature describing numerous and varying combinations of antimicrobial agents for H. pylori eradication, to a large extent due to the fact that it is difficult to predict clinically which combination might work and which will be unsuccessful. Indeed, persons skilled in the art cannot—from in vitro studies or from their previous experience—simply predict the success or failure of a particular regime.

Rifampicin is an antimycobacterial antibiotic used in the treatment of tuberculosis. Recently, its semi-synthetic derivative, an ansamycin called rifabutin which is currently indicated for the treatment of tuberculosis or Mycobacterium avium complex infection, has been described as having in vitro activity against Helicobacter pylori when tested in culture. In the present invention combinations containing an ansamycin have been found to be clinically effective in eradicating H. pylori.

In a first embodiment, the present invention provides a pharmaceutical composition for the treatment of gastrointestinal disorders associated with H. pylori infection including a first antibiotic which is an ansamycin, at least one second antibiotic or antimicrobial agent selected from amoxycillin, tetracycline and bismuth compounds, and a proton pump inhibitor, together with at least one pharmaceutical acceptable carrier, diluent, adjuvant or excipient; wherein said ansamycin is rifabutin.

In a second embodiment, the invention provides a method for the treatment and/or prevention of recurrence of a gastrointestinal disorder associated with H. pylori in a patient requiring said treatment and/or prevention, which method comprises administering to said patient sequentially or simultaneously a therapeutically effective amount of a first antibiotic which is an ansamycin, a therapeutically effective amount of at least one second antibiotic or antimicrobial agent selected from amoxycillin, tetracycline and bismuth compounds, and a therapeutically effective amount of a proton pump inhibit; wherein said ansamycin is rifabutin.

Typically, a method of treatment in accordance with the invention results in the eradication of H. pylori from the patient who is treated.

In a third embodiment, the invention further provides the of a therapeutically effective amount of a first antibiotic which is an ansamycin, a therapeutically effective amount of at least one second antibiotic or antimicrobial agent selected from amoxycillin, tetracycline and bismuth compounds, and a therapeutically effective amount of a proton pump inhibitor for the manufacture of a medicament for the treatment and/or prevention of recurrence of a gastrointestinal disorder associated with H. pylori in a patent; wherein said ansamycin is rifabutin.

In a fourth embodiment, the invention still further provides a therapeutically effective amount of a first antibiotic which is an ansamycin and a therapeutically effective amount of at least one second antibiotic or antimicrobial agent selected from amoxycillin, tetracycline and bismuth compounds, and a therapeutically effective amount of a proton pump inhibitor when used for the treatment and/or prevention of recurrence of a gastrointestinal disorder associated with H. pylori in a patient; wherein said ansamycin is rifabutin.

The pharmaceutical composition of the invention includes, in addition to the ansamycin, one or more other antibiotics or antimicrobial agents. Typically, where the patient to whom the pharmaceutical composition is to be administered has previously not been treated for H. pylori infection, the pharmaceutical composition of the invention includes rifabutin, and just one other antibiotic or antimicrobial agent. In other cases, the pharmaceutical composition typically includes rifabutin, and two different antibiotics or antimicrobial agents.

Similarly, in the method of the second embodiment and in the third and fourth embodiments of the invention the ansamycin and a single other antibiotic or antimicrobial agent may be used, but more typically the ansamycin and two different other antibiotics or antimicrobial agents may be used.

In the method of the second embodiment, the active agents, namely the ansamycin, the one or more other antibiotics or antimicrobial agents, and the proton pump inhibitor may be administered simultaneously or sequentially, in any order.

The pharmaceutical composition of the first embodiment includes a proton pump inhibitor (PPI). Similarly, a method of the second embodiment includes the administration of a proton pump inhibitor. The inclusion of a PPI can help to enhance the eradication rate of *H. pylori* and can improve the patient's symptoms, since patients are often dyspeptic at the beginning of the treatment. The administration of the PPI in the method of the second embodiment may be separate from the administration of the ansamycin and other antibiotic(s) or antimicrobial agent(s), or the PPI may be co-administered with the ansamycin and/or one or more other antibiotics or antimicrobial agents. Suitable PPIs include omeprazole, pantoprazole, Iansoprazole and rabeprazole.

The antibiotic(s) or antimicrobial agent(s) included in the pharmaceutical composition, method or use of the invention may be selected from amoxycillin, bismuth compounds and tetracycline. Examples of bismuth compounds include bismuth subcitrate, bismuth aluminate, bismuth oxide, bismuth salicylate, bismuth sugballate, bismuth tannate, bismuth phosphate, bismuth tribromphenate, bismuth subcarbonate, bismuth subnitrate, and mixtures thereof.

Typically, in one form of the invention rifabutin is used in combination with pantoprazole, amoxycillin and a bismuth compound. An alternative second antimicrobial agent in this form of the invention is a tetracycline.

One preferred combination for use in the pharmaceutical compositions, methods and other embodiments of the present invention in patients who do not harbour resistant *H. pylori* is a combination of rifabutin, amoxycillin and a PPI such as omeprazole, pantoprazole or lansoprazole. A further preferred combination is a combination of rifabutin, tetracycline and pantoprazole. These combinations can be given for between three and 21 days to affect a cure.

In another combination, rifabutin can be combined with a bismuth compound and pantoprazole.

In a further combination rifabutin can be combined with bismuth subcitrate, amoxycillin, and a PPI such as pantoprazole or omeprazole. This combination has the added advantage that the dosage of each agent can be reduced, compared to clinically standard doses (with a reduction in the possibility of side effects as well as a reduction in cost) and the duration of treatment shortened, for example to 7 days.

Pharmaceutical compositions of the invention include one or more pharmaceutically acceptable excipients, adjuvants, diluents or carriers which are generally known in the art.

Pharmaceutical compositions of the invention or for administration in a method of the invention may be prepared by means known in the art for the preparation of pharmaceutical compositions including blending, grinding, homogenising, suspending, dissolving, emulsifying, dispersing and where appropriate, mixing of the active agents together with one or more excipients, diluents, carriers and adjuvants.

For oral administration, the pharmaceutical composition may be in the form of tablets, lozenges, pills, troches, capsules, elixirs, powders, including lyophilised powders, solutions, granules, suspensions, emulsions, syrups and tinctures. Slow-release, or delayed-release, forms may also be prepared, for example in the form of coated particles, multi-layer tablets or microgranules.

Solid forms for oral administration may contain pharmaceutically acceptable binders, sweeteners, disintegrating agents, diluents, flavourings, coating agents, preservatives, lubricants and/or time delay agents. Suitable binders include gum acacia, gelatin, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the active agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further include dispersing agents and/or suspending agents. Suitable suspending agents include sodium carboxymethylcellulose, methylcellulose, hydroxypropylmethyl-cellulose, polyvinyl-pyrrolidone, sodium alginate or cetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

Emulsions for oral administration may further include one or more emulsifying agents. Suitable emulsifying agents include dispersing agents as exemplified above or natural gums such as gum acacia or gum tragacanth.

Dosages of the ansamycin and the other antibiotic(s) or antimicrobial agent(s) in the methods of the invention are in accordance with their generally known and safe dosage ranges. For example, dosages for the antimicrobial agents are well known to medical practitioners, as are suitable dosages for rifabutin when it is administered for the treatment of tuberculosis or *Mycobacterium avium* complex infection. Thus, for example the typical daily dosage of rifabutin in a method of the invention is in the range of about 50 mg to about 2000 mg, more typically about 450 mg. For tetracycline the typical daily dosage is in the range of from about 50 mg to about 4000 mg, more typically about 1500 mg; for amoxycillin, the typical daily dosage is in the range of from about 100 mg to about 5000 mg, more typically about 1500 mg; for bismuth the typical daily dosage is in the range of from about 50 mg to about 2000 mg, more typically about 300 mg; and for pantoprazole the typical daily dosage is in the range of from about 20 mg to about 500 mg, more typically about 120 mg.

The agents may be administered once per day or more frequently, in divided doses. For example, rifabutin can be administered from twice daily up to five times daily. Treatment is typically continued until eradication of the *H. pylori* infection has been completed. Usually, the treatment is continued for from three days to 14 days, but can continue for up to 28 days. Dosages may be varied during the course of treatment, depending on the attending physician's assessment of the progress of the patient, or they may be maintained substantially the same throughout the treatment.

In addition, for resistant strains the patient can be pretreated with known immunising agents for *Helicobacter pylori* and then treated with any selected combination of the rifabutin-containing combination therapies of the present invention.

EXAMPLES

Example 1

The Table presents the results of testing carried out on a number of patients using the epsilon test ("E-test", AB Biodisc) which show that in all cases where there was infection by *H. pylori* which was resistant to one or both of metronidazole and clarithromycin, the infection was sensitive to rifabutin administration. The E-test is used as a graded antibiotic sensitivity detecting strip for examining resistance of *H.pylori*.

Example 2

A male patient, 37 years old, who had been unsuccessfully treated previously for *H. pylori* infection using a combination of clarithromycin, amoxycillin and omeprazole was treated by administration of 4 times daily doses of rifabutin, pantoprazole and tetracycline in amounts of 600 mg, 160 mg and 2000 mg per day respectively. After a period of 8 days on this treatment, the *H. pylori* infection in the patient had been eradicated.

TABLE

E. Test for Metronidazole, Clarithromycin and Rifabutin

| Patient | | | | Urease test | Culture | E. Test | | | | | |
|---|---|---|---|---|---|---|---|---|---|---|---|
| | | | | for | for | Metronidazole | | Clarithromycin | | Rifabutin | |
| ID. | Initials | Age | Sex | *H. pylori* | *H. pylori* | ug/mL | Result | ug/mL | Result | g/mL | Result |
| 1 | FA | 27 | m | Positive | 3 | >32 | Resistant | <0.016 | Sensitive | N/A | N/A |
| 2 | MJ | 59 | m | Positlve | 3 | >32 | Resistant | <0.016 | Sensitive | N/A | N/A |
| 3 | KJ | 61 | f | Positive | 3 | >32 | Resistant | <0.016 | Sensitive | N/A | N/A |
| 4 | YW | 59 | m | Positive | 3 | >32 | Resistant | <0.016 | Sensitive | N/A | N/A |
| 5 | TD | 60 | f | Positive | 2 | >32 | Resistant | <0.016 | Sensitive | N/A | N/A |
| 6 | BL | 34 | f | Positive | 2 | >32 | Resistant | <0.016 | Sensitive | N/A | N/A |
| 7 | AB | 67 | m | Positive | 1 | >32 | Resistant | <0.016 | Sensitive | N/A | N/A |
| 8 | RR | 59 | f | Positive | 1 | N/A | N/A | <0.016 | Sensitive | <0.002 | Sensitive |
| 9 | CH | 81 | m | Positive | 2 | N/A | N/A | N/A | N/A | <0.002 | Sensitive |
| 10 | AA | 71 | m | Positive | 3 | N/A | N/A | <0.016 | Sensitive | <0.002 | Sensitive |
| 11 | W | 58 | m | Positive | 2 | N/A | N/A | <0.016 | Sensitive | <0.002 | Sensitive |
| 12 | PM | 40 | f | Positive | 2 | N/A | N/A | <0.016 | Sensitive | <0.002 | Sensitive |
| 13 | OL | 52 | f | Positive | 2 | N/A | N/A | <0.016 | Sensitive | <0.002 | Sensitive |
| 14 | HS | 29 | f | Positive | 2 | N/A | N/A | <0.016 | Sensitive | <0.002 | Sensitive |
| 15 | FJ | 42 | m | Positive | 2 | N/A | N/A | <0.016 | Sensitive | <0.002 | Sensitive |
| 16 | MG | 56 | m | Positive | 1 | N/A | N/A | <0.016 | Sensitive | <0.002 | Sensitive |
| 17 | HC | 52 | f | Positive | 3 | N/A | N/A | <0.016 | Sensitive | <0.002 | Sensitive |
| 18 | CL | 43 | m | Positive | 2 | N/A | N/A | <0.016 | Sensitive | <0.002 | Sensitive |
| 19 | SR | 52 | m | Positive | 2 | N/A | N/A | <0.016 | Sensitive | <0.002 | Sensitive |
| 20 | WJ | 66 | m | Positive | 1 | N/A | N/A | <0.016 | Sensitive | <0.002 | Sensitive |
| 21 | DN | 58 | f | Positive | 3 | N/A | N/A | <0.016 | Sensitive | <0.002 | Sensitive |
| 22 | DF | 26 | m | Positive | 3 | N/A | N/A | <0.016 | Sensitive | <0.002 | Sensitive |
| 23 | HM | 39 | m | Positive | 3 | >32 | Resistant | >4 | Resistant | <0.002 | Sensitive |
| 24 | LL | 22 | f | Positive | 3 | >32 | Resistant | <0.016 | Sensitive | <0.002 | Sensitive |
| 25 | DJ | 48 | f | Positive | 2 | >32 | Resistant | <0.016 | Sensitive | <0.002 | Sensitive |
| 26 | BM | 52 | f | Positive | 3 | >32 | Resistant | <0.016 | Sensitive | <0.002 | Sensitive |
| 27 | EHK | 32 | f | Positive | 3 | >32 | Resistant | <0.016 | Sensitive | <0.002 | Sensitive |
| 28 | FM | 63 | f | Positive | 3 | >32 | Resistant | <0.016 | Sensitive | <0.002 | Sensitive |
| 29 | MM | 27 | m | Positive | 3 | >32 | Resistant | <0.016 | Sensitive | <0.002 | Sensitive |
| 30 | HF | 55 | m | Positive | 3 | >32 | Resistant | <0.016 | Sensitive | <0.002 | Sensitive |
| 31 | BA | 41 | m | Positive | 3 | >32 | Resistant | <0.016 | Sensitive | <0.002 | Sensitive |
| 32 | LIS | | | Positive | 3 | >32 | Resistant | <0.016 | Sensitive | <0.002 | Sensitive |
| 33 | IN | | | Positive | 2 | >32 | Resistant | <0.016 | Sensitive | <0.002 | Sensitive |
| 34 | PJ | | | Positive | 2 | >32 | Resistant | <0.016 | Sensitive | <0.002 | Sensitive |
| 35 | TH | | | Positive | 3 | >32 | Resistant | <0.016 | Sensitive | <0.002 | Sensitive |
| 36 | FE | | | Positive | 3 | >32 | Resistant | <0.016 | Sensitive | <0.002 | Sensitive |
| 37 | BN | 72 | f | Positive | 3 | >32 | Resistant | <0.016 | Sensitive | <0.002 | Sensitive |
| 38 | AM | 62 | m | Positive | 3 | >32 | Resistant | <0.016 | Sensitive | <0.002 | Sensitive |
| 39 | TR | 56 | m | Positive | 3 | >32 | Resistant | <0.016 | Sensitive | <0.002 | Sensitive |
| 40 | GJ | 64 | f | Positive | 2 | >32 | Resistant | <0.016 | Sensitive | <0.002 | Sensitive |
| 41 | HE | 91 | f | Positive | 1 | >32 | Resistant | <0.016 | Sensitive | <0.002 | Sensitive |
| 42 | HA | 51 | m | Positive | 3 | <0.125 | Sensitive | <0.016 | Sensitive | <0.002 | Sensitive |
| 43 | LE | 40 | m | Positive | 1 | >32 | Resistant | <0.016 | Sensitive | <0.002 | Sensitive |

TABLE-continued

E. Test for Metronidazole, Clarithromycin and Rifabutin

| Patient | | | | Urease test for *H. pylori* | Culture for *H. pylori* | E. Test | | | | | |
|---|---|---|---|---|---|---|---|---|---|---|---|
| | | | | | | Metronidazole | | Clarithromycin | | Rifabutin | |
| ID. | Initials | Age | Sex | | | ug/mL | Result | ug/mL | Result | g/mL | Result |
| 44 | CE | 77 | f | Positive | 3 | >32 | Resistant | <0.016 | Sensitive | <0.002 | Sensitive |
| 45 | MG | 74 | f | Positive | 3 | >32 | Resistant | <0.016 | Sensitive | <0.002 | Sensitive |
| 46 | GP | 79 | f | Positive | 3 | >32 | Resistant | <0.016 | Sensitive | <0.002 | Sensitive |
| 47 | BD | 73 | f | Positive | 2 | >32 | Resistant | <0.016 | Sensitive | <0.002 | Sensitive |
| 48 | MC | 31 | f | Positive | 2 | <2 | Sensitive | <0.016 | Sensitive | <0.002 | Sensitive |
| 49 | LJ | 58 | m | Positive | 3 | >4 | Resistant | <0.016 | Sensitive | <0.002 | Sensitive |
| 50 | IE | 49 | f | Positive | 2 | N/A | N/A | N/A | N/A | N/A | N/A |
| 51 | AM | 64 | m | Positive | 3 | N/A | N/A | N/A | N/A | N/A | N/A |
| 52 | PG | 64 | f | Positive | 1 | >32 | Resistant | <0.016 | Sensitive | <0.002 | Sensitive |

*1: light    2: medium    3: heavy
N/A: results not available

What is claimed is:

1. A pharmaceutical composition for the treatment of gastrointestinal disorders associated with *H. pylori* infection including a first antibiotic which is an ansamycin, at least one second antibiotic or antimicrobial agent selected from the group consisting of amoxycillin, tetracycline and bismuth compounds, and a proton pump inhibitor, together with at least one pharmaceutical acceptable carrier, diluent, adjuvant or excipient; wherein said ansamycin is rifabutin.

2. A pharmaceutical composition according to claim 1, wherein the proton pump inhibitor is selected from the group consisting of omeprazole, pantoprazole, rabeprazole and lansoprazole.

3. A pharmaceutical composition according to claim 2, wherein the proton pump inhibitor is pantoprazole.

4. A pharmaceutical composition according to claim 1, wherein said second antibiotic or antimicrobial agent is tetracycline.

5. A pharmaceutical composition according to claim 1, wherein said second antibiotic or antimicrobial agent is amoxycillin.

6. A pharmaceutical composition according to claim 1, wherein said second antibiotic or antimicrobial agent is a bismuth compound.

7. A method for the treatment of a gastrointestinal disorder associated with *H. pylori* in a patient requiring said treatment, which method comprises administering to said patient sequentially or simultaneously a therapeutically effective amount of a first antibiotic which is an ansamycin, a therapeutically effective amount of at least one second antibiotic or antimicrobial agent selected from the group consisting of amoxycillin, tetracycline and bismuth compounds, and a therapeutically effective amount of a proton pump inhibitor; wherein said ansamycin is rifabutin.

8. A method according to claim 7, wherein said proton pump inhibitor is selected from omeprazole, pantoprazole, rabeprazole and lansoprazole.

9. A method according to claim 8, wherein said proton pump inhibitor is pantoprazole.

10. A method according to claim 7, wherein said second antibiotic or antimicrobial agent is tetracycline.

11. A method according to claim 7, wherein said second antibiotic or antimicrobial agent is amoxycillin.

12. A method according to claim 7, wherein said second antibiotic or antimicrobial agent is a bismuth compound.

13. A composition comprising a therapeutically effective amount of a first antibiotic which is an ansamycin and a therapeutically effective amount of at least one second antibiotic or antimicrobial agent selected from the group consisting of amoxycillin, tetracycline and bismuth compounds, and a therapeutically effective amount of a proton pump inhibitor when used for the treatment of a gastrointestinal disorder associated with *H. pylori* in a patient; wherein said ansamycin is rifabutin.

14. A composition comprising a therapeutically effective amount of a first antibiotic which is rifabutin and a therapeutically effective amount of a least one second antibiotic or antimicrobial agent selected from the group consisting of amoxycillin, tetracycline and bismuth compounds, and a therapeutically effective amount of a proton pump inhibitor selected from the group consisting of omeprazole, pantoprazole, rabeprazole and lansoprazole, when used for the treatment of a gastrointestinal disorder associated with *H. pylori* in a patient.

15. A composition comprising a therapeutically effective amount of a first antibiotic which is rifabutin and a therapeutically effective amount of a least one second antibiotic or antimicrobial agent selected from the group consisting of amoxycillin, tetracycline and bismuth compounds, and a therapeutically effective amount of pantoprazole when used for the treatment of a gastrointestinal disorder associated with *H. pylori* in a patient.

16. A composition comprising a therapeutically effective amount of rifabutin and a therapeutically effective amount of tetracycline and a therapeutically effective amount of a proton pump inhibitor when used for the treatment of a gastrointestinal disorder associated with *H. pylori* in a patient.

17. A composition comprising a therapeutically effective amount of rifabutin and a therapeutically effective amount of amoxycillin and a therapeutically effective amount of a proton pump inhibitor when used for the treatment of a gastrointestinal disorder associated with *H. pylori* in a patient.

18. A composition comprising a therapeutically effective amount of rifabutin and a therapeutically effective amount of a bismuth compound and a therapeutically effective amount of proton pump inhibitor when used for the treatment of a gastrointestinal disorder associated with *H. pylori* in a patient.

* * * * *